(12) United States Patent
Barbeau et al.

(10) Patent No.: US 11,085,083 B2
(45) Date of Patent: Aug. 10, 2021

(54) METHODS TO DETERMINE CARCINOGENESIS, IDENTIFY MARKERS FOR EARLY CANCER DIAGNOSIS AND IDENTIFY TARGETS OF THERAPY

(71) Applicants: James M. Barbeau, New Orleans, LA (US); John S. DePaolo, New Orleans, LA (US)

(72) Inventors: James M. Barbeau, New Orleans, LA (US); John S. DePaolo, New Orleans, LA (US)

(73) Assignee: VISIBLE GENOMICS, LLC, Cincinnati, OH (US)

( * ) Notice: Subject to any disclaimer, the term of this patent is extended or adjusted under 35 U.S.C. 154(b) by 186 days.

(21) Appl. No.: 14/217,822

(22) Filed: Mar. 18, 2014

(65) Prior Publication Data

US 2014/0274742 A1    Sep. 18, 2014

Related U.S. Application Data

(60) Provisional application No. 61/802,788, filed on Mar. 18, 2013.

(51) Int. Cl.
*C12Q 1/6886* (2018.01)
*G16B 20/00* (2019.01)

(52) U.S. Cl.
CPC .......... *C12Q 1/6886* (2013.01); *G16B 20/00* (2019.02); *C12Q 2600/112* (2013.01); *C12Q 2600/158* (2013.01)

(58) Field of Classification Search
CPC .................................................. C12Q 1/6886
See application file for complete search history.

(56) References Cited

U.S. PATENT DOCUMENTS

| | | | |
|---|---|---|---|
| 5,420,911 A | 5/1995 | Dahlin et al. | |
| 7,412,333 B2 | 8/2008 | Shackney | |
| 2002/0048766 A1* | 4/2002 | Doyle | C12Q 1/6841 435/6.12 |
| 2003/0165895 A1* | 9/2003 | Czerniak | C12Q 1/6886 435/6.18 |
| 2008/0064049 A1 | 3/2008 | Clarke et al. | |
| 2008/0207714 A1 | 8/2008 | Chinnaiyan et al. | |
| 2009/0117549 A1 | 5/2009 | Tan et al. | |

(Continued)

OTHER PUBLICATIONS

Richards et al. (2007) "A microaliquoting technique for precise histological annotation and optimization of cell content in frozen tissue specimens." Biotechnic & Histochemistry 82(4-5):189-197.*

(Continued)

*Primary Examiner* — Jeremy C Flinders
(74) *Attorney, Agent, or Firm* — Jason P. Mueller; FisherBroyles, LLP

(57) ABSTRACT

Methods and techniques to identify carcinogenesis pathways and markers for early cancer diagnosis. Cell sampling is performed on a single tumor with multiple samples being taken from the tumor and outward toward the periphery and beyond. Large scale analysis is performed, such as whole genomic sequencing, to identify the differences between the cells of the various samples. The differences are evaluated to determine which differences represent a change along the carcinogenesis pathway.

10 Claims, 2 Drawing Sheets

(56) References Cited

U.S. PATENT DOCUMENTS

| | | |
|---|---|---|
| 2010/0330567 A1 | 12/2010 | Hoon et al. |
| 2011/0250608 A1 | 10/2011 | Patel et al. |
| 2012/0077682 A1 | 3/2012 | Bowcock et al. |
| 2012/0101002 A1 | 4/2012 | Riel-Mehan et al. |
| 2012/0143805 A1 | 6/2012 | Gold et al. |
| 2012/0214880 A1 | 8/2012 | Backman et al. |
| 2012/0238463 A1 | 9/2012 | Goel et al. |
| 2012/0288879 A1 | 11/2012 | Altiok |

OTHER PUBLICATIONS

Tabor et al. (2002) "Multiple head and neck tumors frequently originate from a single preneoplastic lesion." American Journal of Pathology 161(3):1051-1060.*

Kerick et al. (2011) "Targeted high throughput sequencing in clinical cancer settings: formaldehyde fixed-paraffin embedded (FFPE) tumor tissues, input amount and tumor heterogeneity" BMC Medical Genomics 4:68.*

Gui et al. (2011) "Frequent mutations of chromatin remodeling genes in transitional cell carcinoma of the bladder" Nature Genetics 43(9): 875-878.*

Ukai et al (2010) "Transurethral resection in one piece (TURBO) is an accurate tool for pathological staging of bladder tumor" Int. J. Urology 17(8):708-714.*

Guo et al. (2012) "Microdissection of spatially identified single nuclei in a solid tumor for single cell whole genome sequencing" BioTechniques 52(4):1-3.*

Nicholas Navin et al: "Tumour evolution inferred by single—cell sequencing", Nature, vol. 472, No. 7341, Mar. 13, 2011 (Mar. 13, 2011), pp. 90-94, XP055042936, ISSN: 0028-0836.

Wellmann Axel et al: "Analysis of microdissected prostate tissue with ProteinChip(R) arrays: A way to new insights into carcinogenesis and to diagnostic tools", International Journal of Molecular Medicine, Spandidos Publications, GR, vol. 9, No. 4, Apr. 1, 2002 (Apr. 1, 2002), pp. 341-347, XP009091922, ISSN: 1107-3756.

Yamabuki Takumi et al: "Genome-Wide Gene Expression Profile Analysis of Esophageal Squamous Cell Carcinomas", International Journal of Oncology, Demetrios A. Spandidos Ed. & Pub, GR, vol. 28, No. 6, Jan. 1, 2006 (Jan. 1, 2006), pp. 1375-1384, XP009074902, ISSN: 1019-6439.

Zhou Jin et al: "Gene expression profiles at different stages of human esophageal squamous cell carcinoma", World Journal of Gastroenterology, WJG Press, CN, vol. 9, No. 1, Jan. 1, 2003 (Jan. 1, 2003) pp. 9-15, XP002334878, ISSN: 1007-9327.

Kitahara 0 et al: "Alterations of gene expression during colorectal carcinogenesis revealed by cDNA microarrays after laser-capture microdissection of tumor tissues and normal epithelia", Cancer Research, American Association for Cancer Research, US, vol. 61, No. 9, May 1, 2001 (May 1, 2001), pp. 3544-3549, XP002267611, ISSN: 0008-5472.

Jacqueline A. Brosnan et al: "A new branch on the tree: Next-generation sequencing in the study of cancer evolution", Seminars in Cell & Developmental Biology, vol. 23, No. 2, Jan. 8, 2012 (Jan. 8, 2012), pp. 237-242, XP055042935, ISSN: 1084-9521.

* cited by examiner

METHODS TO DETERMINE CARCINOGENESIS, IDENTIFY MARKERS FOR EARLY CANCER DIAGNOSIS AND IDENTIFY TARGETS OF THERAPY

CROSS-REFERENCE TO RELATED APPLICATIONS

The present application claims the benefit of U.S. Provisional Patent Application No. 61/802,788 filed Mar. 18, 2013, which is incorporated herein by reference.

FIELD

The present disclosure relates generally to cancer progression analysis, and in exemplary though non-limiting embodiments, to novel methods for revealing cellular alterations characteristic of cancers.

BACKGROUND

The war on cancer is now more than 40 years old. During this time of unprecedented public and private spending on healthcare research, the scientific community has made significant advances. Many of the pathways and proteins that play important roles in cancer are now known and a portion of these have been therapeutically targeted with varying degrees of success. Cancer researchers have given patients a reason to hope for the future of cancer care. Despite these advances, the underlying causes of carcinogenesis (cancer development) remain substantially unknown.

It is widely recognized that cancer is most treatable and/or curable at its earliest stages; for example, late dysplasia and carcinoma in situ are far more easily addressed than fulminant, possibly metastatic cancer. However, most cancer research today investigates established tumors to discern common pathway genes that are mutated in a high proportion of patients. This approach may have significant flaws. First, there is no evidence that commonly found mutations are initiators of carcinogenesis. Mutations found may occur only in final stages of tumorigenesis, making said mutations relatively poor diagnostic and therapeutic targets. For example, most cancers have a mutation or down-regulation of p53, an enormously important tumor suppressor; however, this alteration occurs in late stages of tumor development. From a therapeutic or diagnostic perspective, this mutation or down-regulation of p53 may have limited relevance.

It is well established that multiple, cumulative genetic changes are usually involved in cancer development. These changes may occur either due to exposure to a carcinogen, or from gene replication mistakes that naturally occur and occasionally evade the cell's self-monitoring systems. What is less understood is which genetic changes are most important, and which mutations occur earliest in the tumorigenic process. Also unknown is what kind of genetic or epigenetic changes occur within a cell that might create the conditions for other, more definitive pre-malignant mutations to develop. For instance, changes in the pattern of DNA methylation in certain gene promoter regions may precede a primary mutation that initiates a tumorigenic process. If early changes in the tumorigenic process can be identified, researchers may begin to design tests to recognize early stage tumor biomarkers and create novel, targeted therapeutics directed at early and/or essential genetic changes.

Under typical methods of cancer research, an important limitation or flaw may arise from sampling concepts or techniques. Studies have shown that cell populations within tumors are increasingly heterogeneous as tumor size increases. For example, renal cell carcinomas contain diverse clonal populations within fully developed tumors, as demonstrated when the same renal tumor is sequenced multiple times. This fact has worrisome implications about the utility of isolated genomic information from randomly sampled fulminant tumors. From a research perspective, there is reason to doubt whether one tumor sample or even a variety of samples in an established carcinoma can be used to identify fundamental and therapeutically important genetic alterations that lead to carcinogenesis. Under current methodologies, researchers may actually be building complex databases that are incapable of revealing important information about carcinogenesis no matter how sophisticated future bioinformatic techniques become.

Typically, efforts to identify important genetic changes in cancer using genomic information have focused on sampling advanced stage tumors in multiple individuals and submitting sequence information (sometimes full genomes but more often incomplete sequencing data) to growing databases. As such, there is a rapidly growing burden of data that includes genomic information about tumors that have already reached a critical level of proliferative capacity and high mutation rates. Bioinformatics is being asked to discern the most important mutations based upon statistical information such as prevalence of mutations without identifying the causative nature of mutations or their locations along the carcinogenesis pathway. Aggregation of such data has generally failed to demonstrate which genetic changes occur early in a natural history of tumors, or the significance of changes or mutations that follow.

With costs of large-scale whole genome sequencing precipitously falling (see www.genome.gov/sequencingcosts), collection of genomic data may be accomplished more cheaply than previously possible. However, collecting genomic data should be completed in a manner that yields insights, which may, in turn, lead to impactful ways to detect and treat cancer, ideally in the pre-malignant stage, before frank cancer even develops. Current data collection techniques merely identify the presence of biomarkers connected to one or more cancers without identifying or determining the role of a particular biomarker or mutation in the development of cancer. Sample and data collection methods fail to account for early stage changes such as mutations that may be found in dysplastic tissue surrounding a tumor. In fact, even when samples of a tumor are sequenced and compared to non-tumor tissue, comparisons are made to normal tissues in order to identify all of the differences between the normal tissue and the cancerous tissue. No existing methods include precancerous tissue analysis or comparisons between precancerous tissue and the tumor to identify early stage changes. The existing methods create mounds of data but fail to utilize information available in dysplastic tissues. The techniques do not identify mutations or changes occurring early in the carcinogenesis pathway or which biomarkers are early indicators along the pathway before cancer develops.

Accordingly, there is a need for improved methods and techniques to systematically analyze tumors and identify markers for early cancer detection and potential targets for therapy including identifying markers in precancerous tissues.

SUMMARY

In an exemplary embodiment of the present invention, a method of analyzing carcinogenesis of a tumor is provided, including: removing at least a portion of the tumor and a portion of normal tissue surrounding the tumor as a tissue block; flash freezing the tissue block; sectioning the tissue block into a plurality of vertical sections; staining alternating vertical sections with hematoxylin and eosin; collecting cell samples from unstained vertical sections using the stained vertical sections as guides and a microdissector, wherein the cell samples are taken from the normal tissue, from a border region between a pre-neoplastic dysplastic region and the normal tissue, from the pre-neoplastic dysplastic region, and from within the tumor; isolating DNA from the cell samples; preparing a DNA library from the isolated DNA; sequencing the DNA library; aligning sequences obtained from the sequencing; and comparing sequences from the cell samples to identify genetic differences between cell samples taken from different tissue regions. The cell sample taken from the normal tissue is used as a baseline for the comparison between sequences.

In an exemplary embodiment of the present invention, a method of analyzing carcinogenesis of a tumor is provided, including: taking at least one cell sample at a location within the tumor; taking at least one cell sample at a location within a periphery of the tumor; performing large scale analysis on all of the cell samples; and identifying differences between cells of the cell samples. The cell samples may be from a solid tumor. The cell samples may be taken by microdissection. The large scale analysis may be at least one of transcriptome sequencing, microRNA profiling, whole genomic sequencing, and bisulfite sequencing. The cell samples may be taken from a single patient. The differences between the cells of the cell samples may be compared to differences between cells of cell samples taken from at least one other individual. The method may include taking at least one cell sample from normal tissue. Differences between normal tissue cells and precancerous cells may be identified. The method may include determining which of the differences between normal tissue cells and precancerous cells are present in cells within the tumor. The method may include determining which differences between the cells of the cell samples contribute to the carcinogenesis.

In an exemplary embodiment of the present invention, a method of identifying carcinogenesis mutations is provided, including: sampling cells within a tumor; sampling cells at a periphery of the tumor; performing large scale analysis of the samplings of cells; and identifying differences between cells of the cell samples.

In an exemplary embodiment of the present invention, a method of identifying diagnostic markers of cancer is provided, including: sampling cells within a tumor; sampling cells at a periphery of the tumor; performing large scale analysis of the samplings of cells; and identifying differences between cells of the cell samples.

In an exemplary embodiment of the present invention, a method of identifying therapeutic targets of cancer is provided, including: sampling cells within a tumor; sampling cells at a periphery of the tumor; performing large scale analysis of the samplings of cells; and identifying differences between cells of the cell samples.

DETAILED DESCRIPTION

Figure 1:
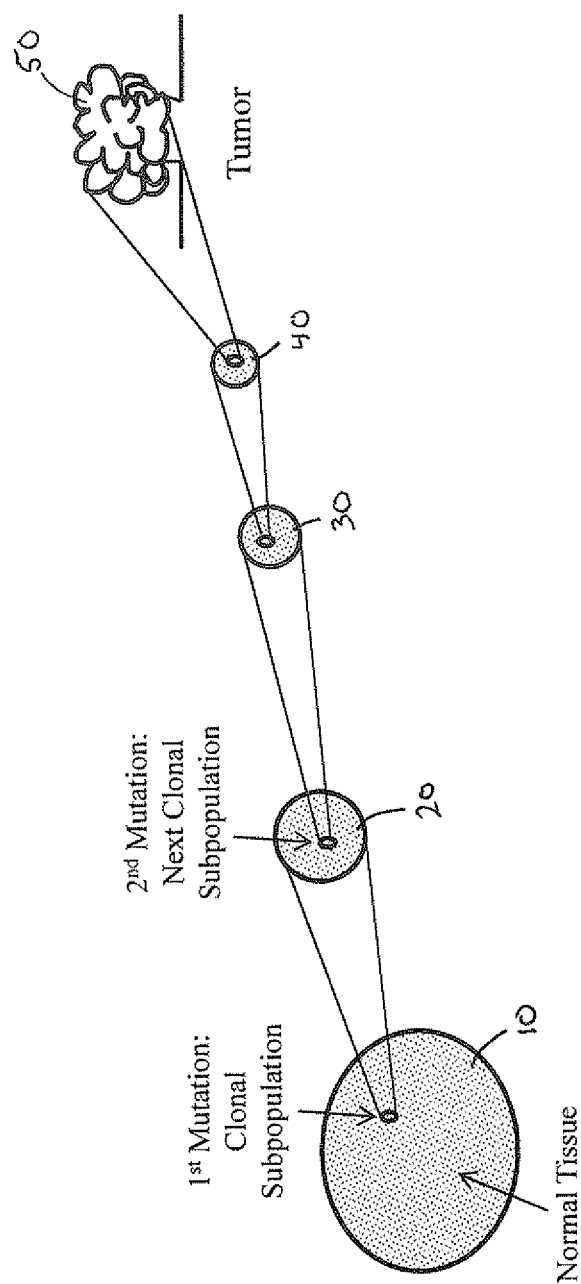
FIG. 1 is a schematic representation of a carcinogenesis pathway showing a series of mutations between a normal tissue and a tumor according to an exemplary embodiment of the present disclosure.

Embodiments of the present invention provide methods for revealing natural histories of cancers. In certain embodiments, the natural histories are revealed by systematically "walking through" individual tumors, performing extensive sampling and analysis from normal cells external to the cancers, through the precursor lesions "peripheral" to the cancers, and finally within the cancers. Embodiments of the present invention provide for progressive sampling of tissues and analysis of data obtained from such progressive sampling such that early stage changes may be identified. Embodiments include subjecting samples to large scale analysis, such as whole genome sequencing (WGS), and comparing data to reveal changes or mutations that occurred during a cancer's evolution. In certain embodiments, known late stage changes and/or mutations may be filtered out using staining techniques or other methods known to identify such late stage changes and then sampling from tissues within a tumor that do not express the late stage change and/or mutation.

Throughout this disclosure, the terms "tumor", "tumor mass", "fulminant tumor", "overt cancer", "frank carcinoma", "frankly malignant neoplasm", "cancer per se", and "cancerous phenotype" are used to indicate an abnormal mass of tissue that has reached a stage of manifesting unregulated cell growth and genetic instability characteristic of malignancy. These terms are intended to distinguish malignant tumors from precursor lesions.

In embodiments of the present invention, techniques involved in acquiring and assaying samples within and peripheral to a tumor mass may proceed as follows: one or more samples of cells may be selected from one or more locations within a mass. Each sample may display varied malignant characteristics, such as differing levels of anaplasia and/or differing nuclear:chromatin ratios. One or more samples of cells may be selected from one or more locations within the dysplastic, precancerous area and progressively further away from the tumor mass. One or more samples of cells may be taken from "normal-appearing" cells surrounding the precancerous area and tumor mass. The samples may be taken at progressively further distances from the tumor mass. Each sample may be submitted for analysis, such as DNA, RNA, and protein analysis. In one embodiment, purified RNA and microRNA may undergo transcriptome sequencing and microRNA profiling. In another embodiment, purified DNA may undergo WGS and bisulfite sequencing. The resulting data may be analyzed against a "normal" sample taken from a significant distance from the tumor mass of the same individual and against each of the other samples, thus allowing the order of cellular changes that occurred throughout tumorigenesis to be determined.

In certain embodiments, a method is disclosed which provides highly efficient discovery of cancer histories. The present invention has increased efficiency compared to prior methods, which typically rely on random sampling of overt tumors from divergent patients and submitting resultant information to central databases for processing. In certain embodiments, the present invention includes extensive sampling through normal-appearing and dysplastic cells at the border of a mass. Beyond the area of dysplasia, it is not yet known how widely the penumbra of borderline genetic changes extends around a solid tumor. It is known that important pre-malignant mutations may not cause any cellular atypia at all. Amounts or extensive nature of sampling in normal-appearing tissue surrounding a neoplasm may be configured and/or adjusted to identify early pre-malignant cells.

Embodiments of the present invention take advantage of the fact that cancers result from cumulative genetic alterations that may lead to an ultimate cancerous phenotype. Populations of pre-cancerous cells may survive in a patient even after subpopulations among those cells acquire new mutations on a carcinogenic pathway. Embodiments of the present invention address carcinogenesis as an iterative process in which mutations create subpopulations that may, in turn, provide starting material for additional mutations. Pathways toward cancer may evolve in this manner while potentially multiple parallel lines may accumulate harmless/neutral mutations. Embodiments of the present invention provide substantial improvement over existing techniques and methods, which target fulminant tissues to identify the prevalence of mutations rather than identifying the order or stage of mutations.

FIG. 1 shows a typical pathway of carcinogenesis. Embodiments of the present invention are designed to reveal the pathway shown in FIG. 1. FIG. 1 illustrates an iterative process whereby mutations accumulate, leading to an ultimate cancerous phenotype. Generally, a genotype that contains all of the mutations that led to the cancerous phenotype is referred to as the tumor's "carcinome." As shown in FIG. 1, a cell(s) of normal tissue 10 undergoes a first mutation forming a subpopulation of cells 20 having the first mutation. Subsequently, a cell(s) of subpopulation 20 undergoes a second mutation forming subpopulation 30 having both the first and second mutations. The process continues through the subpopulation 40 (containing three mutations) and ultimately to the tumor cells (having four mutations in this example). Although shown as a series of four mutations, cancerous cells generally may have twelve or more mutations contributing to the cancerous state. FIG. 1 demonstrates that tumor cells are generally the accumulation of multiple genetic changes and/or mutations, some occurring early in the carcinogenesis pathway and others later in the pathway. Embodiments of the present invention provide methods and techniques to identify the changes and/or mutations that led to each of the subpopulations (20, 30, 40) along the pathway as well as the end tumor cells 50.

Figure 2:
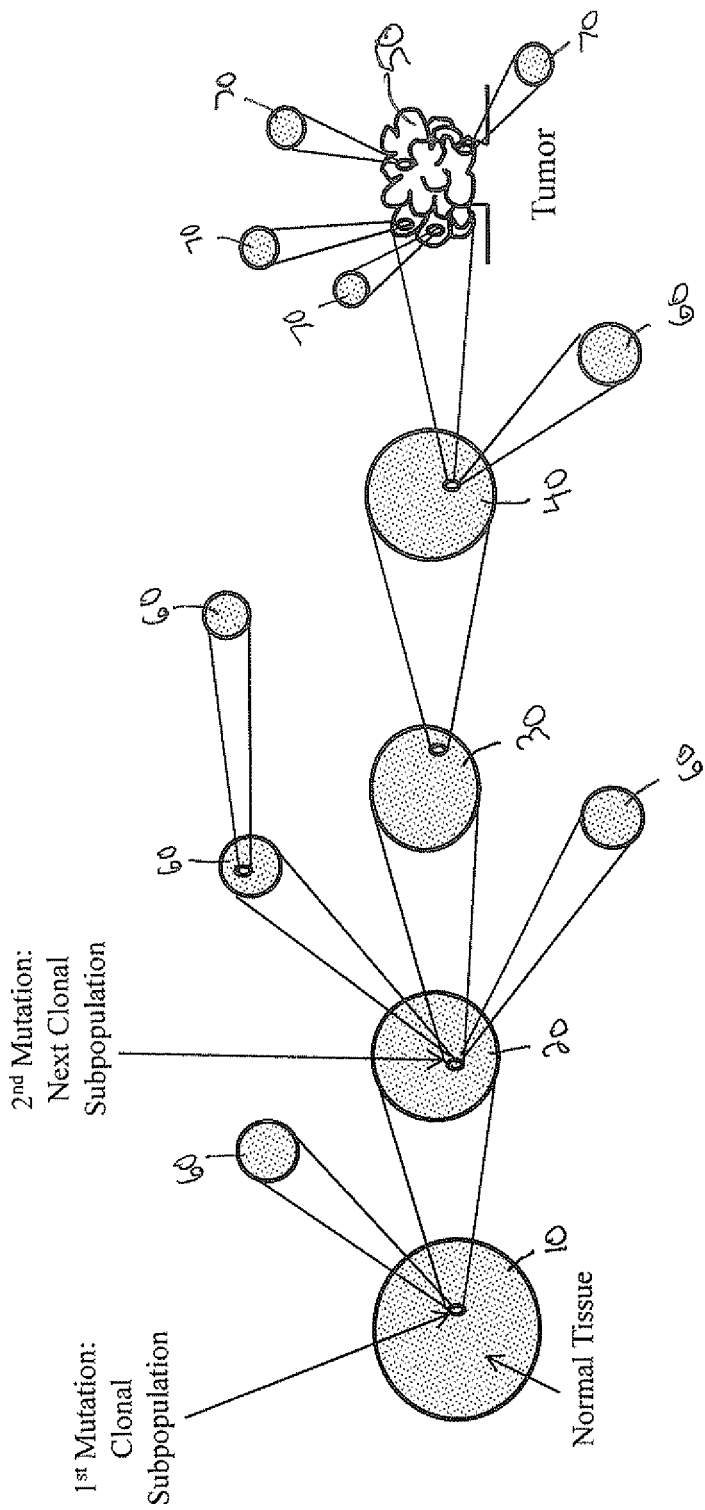
FIG. 2 is a schematic representation of a carcinogenesis pathway showing a series of mutations between a normal tissue and a tumor and showing other non-carcinogenesis pathway mutations according to an exemplary embodiment of the present disclosure.

FIG. 2 is a representation of how mutations typically occur in a natural environment. With the various mutations that lead to the ultimate cancerous phenotype of a given tumor 50, some mutations contribute to carcinogenesis and lead to subpopulations 20, 30 and 40 accumulating driver mutations along the carcinogenesis pathway. Not all mutations in the tumor's carcinome are necessary for carcinogenesis. In addition, some mutations are simply chance occurrences that make no contribution to the development of the cancer (non-pathway mutations). As shown in FIG. 2, clones containing non-pathway mutations produce subpopulations 60, which may also have driver mutations of subpopulations 20, 30, and 40; however the non-pathway mutations do not advance subpopulations 60 along the carcinogenesis pathway. Thus, in addition to mutations that contribute to the carcinome of the malignant tumor, there will also be mutations leading to clonal populations outside the lineage of tumorigenesis. The non-pathway mutations are shown on FIG. 2 as leading away from the path of carcinogenesis. Such lines of mutations that occur outside of the carcinome may be harmless, neutral, or even confer a fitness advantage to the clone, but they do not participate in the evolution of the cancer. These mutations can be an important source of "noise" that distract from identification of the actual carcinome. Embodiments of the present invention effectively filter out such noise allowing for the pertinent mutations along the carcinogenesis pathway to be discovered.

As shown in FIG. 2, typically there are fewer mutations in early carcinogenesis than later stages such as overt cancer. Also, early mutations tend to persist longer and be less prone to variation, extinction, and fixation than those in later stages (e.g. frankly malignant neoplasms). Genetic instability, heterogeneity, and evolutionary progression are generally significantly greater in malignant tumors than in pre-cancerous tissue, making tissue that has reached the neoplastic stage in many ways more difficult to study. Mutations in fulminant tumors may lead to numerous clonal subpopulations 70 having various mutations within said cells, which are not within the primary carcinogenesis pathway (i.e., not within the carcinome). Such later mutations are less likely to provide early markers or early treatment targets. However, continuing to trace the natural history of the tumor beyond the carcinome may reveal diagnostic markers and therapeutic targets that may be useful for treating advanced and metastatic cancer.

In one embodiment, normal cells, pre-cancerous cells, and cells from the tumor are extensively sampled in a single patient using a sampling technique (e.g., microdissection) and each sample is subjected to large scale analysis. In this embodiment, the various samples may act as internal controls for each other. Comparing data will reveal a series of alterations that led to cancer, while other, extraneous changes will "subtract out." Tumor progress may be assessed in both forward and backward directions. Extensive sampling of frank carcinoma within a tumor and working back to the earliest mutations generally will be as informative as proceeding from normal and tracking the accumulation of mutations forward. Knowing changes of malignant cells is similar to knowing an answer to a test question in advance. It permits separation of non-contributory early mutations from mutations that contributed to a tumor's carcinome (i.e., those illustrated in FIG. 1). In contrast to present methods and techniques, sampling is done within a single patient, working through a single tumor and surrounding tissue.

In another exemplary though non-limiting embodiment, one or more samples are taken from the periphery of a tumor and into the fulminant tumor non-discretely, as for example by gross dissection rather than as discrete samples such as one would obtain using microdissection, and analyzed using large-scale analysis such as genomic sequencing to identify cancer evolution by comparing genome subpopulations within the sample or samples. In embodiments of the present invention, upon resection, tumor and surrounding "normal-appearing" tissue may be flash frozen as a tissue block to preserve DNA and RNA. The tissue block may then be sectioned into multiple vertical samples having approximately 5-10 μm thickness and fixated on clean glass histopathology slides with 100% ethanol. Alternating sections may be stained with hematoxylin and eosin (H & E) as a guide for microdissection enabling use of observed cellular characteristics of the stained sections to guide selection of areas for dissection. Samples may be ascertained and collected by use of a laser capture microdissector. One normal sample taken several centimeters from the tumor may be selected as a baseline comparison for genetic analysis. Several samples may be taken from the "normal-appearing" border, pre-neoplastic dysplastic region, and finally from the frank tumor. Once the cell samples are microdissected from frozen tissue, the samples may be immediately digested in proteinase K and placed on ice in buffer. DNA may then be isolated. Sufficient cells are sampled and lysed such that each sample generates at least approximately 2 µg of harvested DNA.

A next-generation whole-genome sequencing platform may be used to create sequencing libraries from the harvested DNA. In one embodiment, approximately 2 µg of DNA from each sample is sheared into 200 bp fragments with an ultrasonicator. DNA may then be end-repaired with $T_4$ DNA polymerase and Klenow polymerase. $T_4$ polynucleotide kinase is used to phosphorylate the 5' ends of the fragments, and a 3' overhang is created with a 3'-5' exonuclease-deficient Klenow fragment. These 3' overhang sticky ends may be ligated to adapter oligonucleotides, as specified by a sequencer manufacturer, and enriched with PCR. Once completed, the quality and size of the DNA library may be confirmed, and the DNA library may be sequenced.

After data is acquired for each sample, sequences may be aligned using Sequence Alignment/Map (SAM) in the paired-end mode as described previously (www.ncbi.nlm.nih.gov/pmc/articles/PMC2723002). The genomic coordinates of these alignments may be analyzed to determine whether the two ends will be aligned to the same chromosome in proper orientation, and mapped to a single location. Once successful alignment is established, inter-sample analysis may be performed to subtract out each new genetic change that occurs between the samples isolated.

In certain embodiments of the present invention, whole genome bisulfite sequencing may be performed in much the same manner as whole genome sequencing using the same instrumentation. Once adapter ligation products are formed as described above, but before the samples are subjected to PCR, the samples may be treated with bisulfite such that each unmethylated cytosine is converted to thymidine. Once these treated samples are purified, they may be subjected to PCR enrichment. Once enriched and purified, clusters are formed in the same manner and samples are subjected to data collection and analysis as described above. SAM tools may be used to align each bisulfite sequence, then data analysis may be performed as described previously (www.ncbi.nlm.nih.gov/pmc/articles/PMC3001746).

Embodiments of the invention disclosed herein may be considered "mining" techniques for essential information regarding carcinogenesis. Due to internal checks provided by the sampling technique, embodiments include methods for simplifying data analysis of cancer genomes. Systematic mining of tumor genomes permits pertinent findings to fall out of genome comparisons. Embodiments of the present invention may also reveal early genetic changes, which may have potential for clinical utility and/or provide cleaner data for evaluating carcinogenic mutations. Because prevention or treatment of cancer may be best addressed at the earliest stages of carcinogenesis, identification of early genetic changes is of vital importance to the potential success of treatments.

Note that embodiments of the present invention may employ large-scale analysis, such as WGS. Large-scale analysis may allow lineages to be traced effectively using markers including, but not limited to, base pair substitutions, insertions, deletions, translocations, gene rearrangements and fusions, copy number alterations, and alterations in microsatellites, STRs, and SNPs, epigenetic changes, or transcriptional changes.

An advantage of the present invention over existing methods and techniques is that embodiments make it unnecessary to know the identities of alterations or mutations in advance. Comparing resulting data may reveal changes that have occurred during evolution of the cancer even if target areas are unknown prior to employing methods of the present invention. This may also have advantages for ascertaining changes in late-stage and metastatic cancer. Additionally, embodiments may also be useful in defining early changes. Identifying biomarkers for detecting cancer in early stages is an important goal of cancer research and is imperative for maximizing treatment options and/or prevention. Developing effective drugs or drug cocktails for the early treatment of cancer is also an important goal. Both efforts may be substantially advanced by improved knowledge obtained with embodiments of the present invention.

In still other embodiments, the present invention may be utilized to compare tumor progression in different patients. Once the evolution of individual tumors has been delineated within individual patients, comparing tumor progression in different patients may yield information on aspects of cancer development such as the prevalence of each cellular event in the pathway toward cancer formation, the identities of driver mutations and passenger mutations, and the relevance of the temporal sequence of carcinogenic events.

In another embodiment, the present invention may be employed to assess progression and/or genesis of leukemias, i.e., cancers of the hematopoietic system. Markers of development of cell lineages of the hematopoietic system are well known, largely as a result of decades-long use of flow cytometry ("cell sorting") for evaluating leukemias. The process of cell sorting by flow cytometry allows populations of cells with characteristic extracellular and intracellular markers to be separated from other cells and represented on scatter plots. Not only may leukemic populations be identified and separated, but also cells on a "periphery" of the leukemia that share, for example, lineage markers with a core leukemic population, but exhibit a slightly different expression of tumor markers. Thus, an embodiment of this invention includes a method for assessing carcinogenesis in leukemia. Embodiments may utilize a wealth of developmental/maturational information known about blood elements, particularly white blood cells, to plan an effective sampling strategy to isolate a normal baseline, various progressively aberrant precancerous changes, and ultimate leukemic population(s), followed by large-scale analysis of separated samples to trace genetic evolution of the leukemia.

In other embodiments, the present invention provides research methods using mammalian model systems, such as rodents or primates, which may be focused on evaluating tumor progression. Embodiments may be useful in investigating tetracycline-inducible mouse models that overexpress certain oncogenes or have conditional knockouts of certain tumor suppressors. For example, once a pattern is established in a study of human colon tumors, and a known oncogene is shown to harbor an initiating mutation, then an inducible mouse model with the same engineered oncogenic mutation present in specific tissue of interest can be established. Embodiments of the present invention may be employed to monitor mice for tumor formation, and simultaneously analyze peripheral blood for tumor-specific DNA. These embodiments may be employed as methods of early detection for carcinogenesis related to colon cancer development due to the oncogenic mutation. Additionally, novel therapeutics may be utilized in such methods to determine effects of early treatment on tumor development and/or eradication. As such, embodiments of the present invention may be used to identify changes associated with tumor progression or in pre-clinical testing of novel therapeutics.

Embodiments of the present invention may be employed to identify cellular changes underlying carcinogenesis in an initial sampling of individuals, ultimately leading to a larger analysis to confirm such changes. For instance, if an initial quantity of patient samples display specific methylation changes in a series of tumor suppressor or oncogene promoters, directed bisulfite sequencing of such specific DNA sequences may be employed on a larger sampling of individuals. This is an improvement over current methods and will prevent the need to submit a large number of individual samples for whole genome bisulfite sequencing. Likewise, if an early structural mutation is found to be prevalent among an initial cohort of patients, such as a translocation that yields a specific fusion protein, an antibody specific for said fusion protein may be used in immunohistochemical analysis of a larger sampling of individuals to better define the prevalence of such a mutation. Collectively, embodiments of the present invention may more rapidly lead to initial identification of cellular changes underlying carcinogenesis, which may ultimately be confirmed in a larger sampling of individuals.

Embodiments described herein may be employed to identify pre-malignant mutations. As illustrated by FIG. 1, mutations typically accumulate iteratively in a series of clonal subpopulations. Each new clone arises out of the previous clone, inheriting cumulative changes that preceded it in addition to its own new mutation(s). A history of cumulative pre-cancerous mutations may surround a tumor like rings of a tree. Extensive sampling around the periphery of many types of tumors may be employed to identify pre-malignant genomes.

Embodiments of the present invention may be employed to identify a genomic evolution of a neoplasm. Regarding the sampling of the tumor mass per se, some pre-malignant and possibly even benign populations may be expected to be admixed in the body of the mass. Some populations within the mass may have evolved beyond an original malignant genotype, possibly developing alternative characteristics including ploidy chromosomal changes, angiogenesis-promotion and metastatic ability (See FIG. 2). Because a fully neoplastic tumor is clonally heterogeneous and genetically unstable, it may be important to define genomic characteristics of several areas within a mass in order to be able to work along a genomic evolution of a neoplasm.

Embodiments may be employed to identify early cancer markers. Embodiments may be employed to identify targets of novel chemotherapeutic agents that may address early-stage carcinomas.

Cancers having precursor lesions may be particularly well suited for embodiments of the present invention. For example, neoplasms such as colon cancer, cervical cancer, breast cancer, lung cancer, cancers arising from Barrett's esophagitis, and many skin cancers are characterized by histologically visible dysplastic pre-cancerous changes. Sampling widely from normal-appearing tissue surrounding such tumors, progressively through dysplastic cells, and into the tumor per se, followed by comparative large-scale analysis, is likely to yield valuable information about the carcinogenesis of these tumors.

Methods described herein may be utilized for detecting epigenetic, exomic, or transcriptional changes throughout a natural history of a tumor. For example, microdissected samples from normal-appearing tissue surrounding a tumor, dysplastic tissue, and frank cancer per se may be subjected to exomic sequencing as well as epigenetic analysis. Samples from normal and dysplastic cells may show, through whole transcriptome analysis, changes in gene expression in key tumor-related genes, as well as genes that do not necessarily contribute to tumorigenesis. Simultaneously, each sample may be analyzed for epigenetic changes. For example, bisulfite sequencing may be used to document changes in methylation. Embodiments may permit observation of significant changes in microRNA regulation, DNA methylation, histone acetylation, etc., including changes in the earliest lesions taken, i.e., lesion furthest removed genetically from frank carcinoma.

Early epigenetic changes may yield noticeable changes in transcriptome when data points from corresponding samples are overlayed. For instance, at a developmental stage prior to the occurrence of a genetic mutation detected by an embodiment of the present invention, increasing methylation in tumor suppressor promoters, with a corresponding downregulation of gene expression is likely to be discovered. Demethylation in promoters of oncogenes, cell cycle-dependent genes, or anti-apoptotic genes, combined with a respective increase in gene expression may also be discovered. Simultaneously, increased expression of microRNAs directed at tumor suppressor transcripts that induce further down-regulation of important protective proteins, or a decrease in expression of microRNAs directed at oncogene transcripts resulting in up-regulation of proliferative proteins may also be observed. Such scenarios pave a way for more rapid cell replication, outstripping cellular checks and balances, whereby chances of a primary carcinogenic mutation become increasingly high. Following an initial tumorigenic mutation, a clonal population of cells more fit to develop into cancer may evolve, and cycles of epigenetic and expression changes may ensue, allowing the formation of clonal populations of cells ripe for additional mutations.

An advantage of the disclosed invention is that it allows documentation of earliest genetic and epigenetic changes that may provide a breeding ground for major DNA mutations, which may lead to tumorigenesis. Such mutations may create new, more cancer-fit clones with different epigenetic regulation and expression profiles, which in turn may contribute to a next carcinogenic mutation. The ability to acquire and overlay data points allows an observer to figuratively "walk through" an individual tumor sample and identify events in its natural history that may have been key to development.

As it is generally believed that 12-15 mutations are necessary to develop true cancer, a three-pronged investigation of microdissected samples may reliably illuminate precise epigenetic, mRNA expression, and structural DNA changes necessary for development of a specific cancer. This new, linear set of data points may be compared with linear data from several other patient tumor samples allowing for an organized way to separate critical steps, or "driver mutations/alterations" from random changes, or "non-pathway mutations/alterations" that occur during the course of tumor development. Cumulative data from a substantial but limited population of patients may provide a basis for developing broad panels of tumor-specific biomarkers and novel early therapies.

While the embodiments are described with reference to various implementations and exploitations, it will be understood that these embodiments are illustrative and that the scope of the invention is not limited to them. Many variations, modifications, additions, and improvements are also possible. Support for the present invention may be found in the attached documents and figures, all of which are expressly incorporated herein in their entirety by reference hereto.

What is claimed is:

1. A method of analyzing carcinogenesis of a single, individual tumor by performing comparative whole genome sequencing on cell samples derived from a tissue block of a tissue sample, the method comprising:
   selecting a selected tissue block, the selected tissue block consisting of individual tumor tissue associated with a single, individual tumor, precursor lesion tissue peripheral to the individual tumor tissue and associated with the single, individual tumor, and normal tissue peripheral to the portion of precursor lesion tissue and associated with the single, individual tumor;
   removing the selected tissue block;
   flash freezing the selected tissue block;
   progressively sectioning the selected tissue block into a plurality of sections, the plurality of sections containing a series of sections containing the normal tissue, a series of sections containing the precursor lesion tissue, and a series of sections containing the individual tumor tissue associated with the single, individual tumor;
   staining alternating sections of the plurality of sections, creating alternating stained and unstained sections;
   characterizing the stained sections as containing one of normal tissue, precursor lesion tissue, and individual tumor tissue;
   collecting cell samples using laser capture microdissection from unstained sections, using the characterized, stained sections as a guide, wherein the collected cell samples include normal tissue cell samples, precursor lesion tissue cell samples, and individual tumor tissue cell samples;
   isolating DNA from the normal tissue cell samples;
   performing whole genome sequencing on DNA isolated from the normal tissue cell samples;
   establishing a genetic baseline derived from the normal tissue cell samples;
   isolating DNA from the precursor lesion tissue cell samples and the individual tumor tissue cell samples;
   performing whole genome sequencing on DNA isolated from the precursor lesion tissue cell samples and the individual tumor tissue cell samples;
   comparing DNA sequence information of the precursor lesion tissue cell samples and the individual tumor tissue cell samples to the genetic baseline derived from the normal tissue cell samples; and
   identifying alterations in the DNA sequence information associated with carcinogenesis based on the comparison of DNA sequence information derived from the precursor lesion tissue cell samples and the individual tumor tissue cell samples as compared to the genetic baseline.

2. The method of claim 1, wherein the plurality of sections are vertical sections.

3. The method of claim 1, wherein the staining is performed with a stain of hematoxylin and eosin.

4. A method of analyzing carcinogenesis of a single, individual tumor, comprising:
   removing a tissue, the tissue including said single, individual tumor and a surrounding tissue surrounding said individual tumor, and selecting and collecting at least one selected tissue block, the selected tissue block consisting of a portion of said single, individual tumor and a portion of the surrounding tissue;
   progressively sectioning the tissue block into a plurality of sections, the plurality of sections including a normal tissue section, a precursor lesion tissue section, and a tumor tissue section;
   dividing alternating tissue sections into at least two populations, the at least two populations including a first population and a second population, and wherein the first population of alternating tissue sections is stained to characterize cells as one of normal, precursor, or tumor cell samples within regions of the first population of alternating tissue sections, and the second population of alternating tissue sections is microdissected using laser capture microdissection using the stained, characterized cells within regions of the first population of alternating tissue sections as a guide to obtain each of an isolated, characterized cell sample derived from tissue characterized as normal tissue, an isolated, characterized cell sample derived from tissue characterized as precursor lesion tissue, and an isolated, characterized cell sample derived from tissue characterized as tumor tissue;
   performing whole genome sequencing on the isolated, characterized cell sample derived from tissue characterized as normal tissue;
   establishing a genetic baseline derived from the isolated, characterized cell sample derived from tissue characterized as normal tissue; and
   performing whole genome sequencing of the isolated, characterized cell samples taken from tissue characterized as precursor lesion tissue and tissue characterized as individual tumor tissue; and
   comparing DNA sequence information of the isolated, characterized cell samples taken from tissue characterized as precursor lesion tissue and tissue characterized as individual tumor tissue to the genetic baseline derived from the isolated, characterized cell sample derived from tissue characterized as normal tissue to identify DNA sequence alterations.

5. The method of claim 4, wherein the selected tissue block is collected by flash freezing.

6. The method of claim 4, wherein the plurality of sections are vertical sections.

7. The method of claim 4, wherein the staining is performed with a stain of hematoxylin and eosin.

8. A method of analyzing carcinogenesis of a single, individual tumor by performing whole genome sequencing on cell samples derived from a tissue block having only one individual tumor, the method comprising:
   selecting a selected tissue block, the selected tissue block consisting of a portion of the single, individual tumor and a portion of surrounding tissue surrounding the single, individual tumor, and wherein the portion of surrounding tissue includes a normal tissue and a precursor lesion tissue;
   removing the selected tissue block;
   progressively sectioning regions of the selected tissue block into a plurality of sections, the plurality of sections including sections of the normal tissue, sections of the precursor lesion tissue, and sections of the tumor tissue;
   separating alternating tissue sections taken from the normal tissue, the precursor lesion tissue, and the individual tumor tissue into a first and second group;
   staining the first group to characterize cells as one of normal, precursor, or tumor cell samples and guide laser capture microdissection of tissue samples of the second group;
   characterizing cell types and collecting cell samples using laser capture microdissection of tissue samples of the second group;

performing whole genome sequencing on the characterized, microdissected cell samples of normal tissue;
establishing a genetic baseline derived from the whole genome sequencing performed on the characterized, microdissected cell samples of normal tissue;
performing whole genome sequencing on the characterized, microdissected cell samples of precursor lesion tissue and individual tumor tissue; and
comparing DNA sequences obtained from the precursor lesion tissue and the individual tumor tissue to the genetic baseline derived from the whole genome sequencing performed on the characterized, microdissected cell samples of normal tissue.

9. A method for analyzing carcinogenesis in a single, individual tumor comprising:
isolating a tissue sample associated with said individual tumor, the tissue sample including a tumor tissue, a precursor lesion tissue surrounding the tumor tissue and associated with the individual tumor, and a normal tissue surrounding the precursor lesion tissue and associated with the individual tumor;
selecting and isolating a selected tissue block from the tissue sample, the selected tissue block comprising each of the normal tissue, the precursor lesion tissue, and the tumor tissue;
progressively sectioning the tissue block to obtain a plurality of tissue sections, wherein the tissue sections comprise at least one of a normal tissue, a precursor lesion tissue, and a tumor tissue;
isolating a plurality of cell samples, the plurality of cell samples comprising at least one cell sample from the normal tissue, at least one cell sample from the precursor lesion tissue, and at least one cell sample from the tumor tissue, wherein the plurality of cell samples are isolated using laser capture microdissection;
performing whole genome sequencing on the at least one isolated cell sample of the normal tissue;
establishing a genetic baseline derived from the at least one isolated cell sample of the normal tissue;
performing whole genome sequencing on the at least one isolated cell sample of the precursor lesion tissue and the individual tumor tissue; and
conducting a comparative sequence analysis to identify sequence alterations between the isolated cell samples of each of the normal tissue, the precursor lesion tissue, and the individual tumor tissue, using the genetic baseline derived from the isolated cell samples of the normal tissue as a baseline.

10. A method for analyzing carcinogenesis in a single, individual tumor comprising:
isolating a tissue sample, the tissue sample having a tumor tissue, a precursor lesion tissue surrounding the tumor tissue and associated with the individual tumor, and a normal tissue surrounding the precursor lesion tissue and associated with the individual tumor;
selecting and isolating a selected tissue block from the tissue sample, the selected tissue block comprising each of the normal tissue, the precursor lesion tissue, and the tumor tissue;
progressively sectioning the tissue block to obtain a plurality of normal tissue sections, precursor lesion tissue sections, and tumor tissue sections;
isolating DNA from cell samples taken from at least one section of normal tissue;
establishing a genetic baseline derived from the isolated DNA of cell samples taken from the at least one section of normal tissue;
isolating DNA from cell samples taken from at least one section of precursor lesion tissue and at least one section of tumor tissue; and
performing comparative large scale analysis on the isolated DNA of cell samples taken from each of the normal tissue, the precursor lesion tissue, and the individual tumor tissue, wherein the genetic baseline derived from the isolated DNA of cell samples taken from the at least one section of normal tissue is used as a baseline in the comparative large scale analysis; wherein said comparative large scale analysis comprises at least one transcriptome sequencing, microRNA profiling, whole genomic sequencing, and bisulfite sequencing.

* * * * *